US006218420B1

(12) United States Patent
Dioguardi

(10) Patent No.: US 6,218,420 B1
(45) Date of Patent: Apr. 17, 2001

(54) COMPOSITIONS BASED ON AMINOACIDS

(75) Inventor: Francesco Saverio Dioguardi, Milan (IT)

(73) Assignee: Professional Dietetics S.r.l., Milan (IT)

( * ) Notice: Subject to any disclaimer, the term of this patent is extended or adjusted under 35 U.S.C. 154(b) by 0 days.

(21) Appl. No.: 09/319,821

(22) PCT Filed: Dec. 16, 1997

(86) PCT No.: PCT/EP97/07051

§ 371 Date: Aug. 2, 1999

§ 102(e) Date: Aug. 2, 1999

(87) PCT Pub. No.: WO98/26774

PCT Pub. Date: Jun. 25, 1998

(30) Foreign Application Priority Data

Dec. 16, 1996 (IT) .................................... 96A1031

(51) Int. Cl.[7] ........................ A61K 31/40; A61K 31/195
(52) U.S. Cl. ........................ 514/419; 514/561; 514/562; 514/567
(58) Field of Search .................... 514/561, 562, 514/419, 567

(56) References Cited

U.S. PATENT DOCUMENTS 4,670,261 * 6/1987 Masayoshi et al. ................. 424/127

FOREIGN PATENT DOCUMENTS

| 25 30 246 | * | 1/1977 | (DE) . |
| 25 31 204 | * | 1/1997 | (DE) . |
| 0 413 528 | * | 2/1991 | (EP) . |
| 63-307822 | * | 12/1988 | (JP) . |
| 3-204814 | * | 9/1991 | (JP) . |
| 82/00411 | * | 2/1982 | (WO) . |

* cited by examiner

Primary Examiner—Raymond Henley, III
(74) Attorney, Agent, or Firm—Levine & Mandelbaum

(57) ABSTRACT

Compositions based or essential aminoacids are described for preventing and treating alimentary overloads in conditions of elevated body nitrogen requirements, without causing calcium losses. In the compositions according to the invention, the ratios among aminoacids are balanced according to the real requirements of human metabolism in order to achieve maximal protein syntheses and, at the same time, minimal catabolic loads. The compositions comprise from 20 to 75% of the branched chain aminoacids, leucine, isoleucine and valine, from 10 to 50% of threonine and lysine, and up to 40% of cistine, hystidine, phenylalanine, and thyrosine, methionine and triptophan.

9 Claims, No Drawings

COMPOSITIONS BASED ON AMINOACIDS

This is a 371 of PCT/EP97/07051 filed Dec. 16, 1997.

DESCRIPTION

The present invention refers to compositions based on aminoacids, for preventing and treating alimentary overloads in conditions of elevate body nitrogen requirements, without causing calcium losses.

It is well known that carbon, oxygen and hydrogen are the atoms that form carbohydrates and lipids being necessary to our metabolic energy requirements.

Nitrogen is instead the component of the structural elements of our body, i.e. the proteins, and must be introduced daily in quantities that should match the daily losses.

While carbohydrates can be transformed only in lipids, proteins can be transformed both in carbohydrates and in lipids, according to body needs, however neither carbohydrates nor lipids can be transformed in proteins (just a minimum quantity and only of some among the chemically simplest aminoacids can be obtained from carbohydrates, involving a very high consumption of body energy).

Thus we depend on an adequate nitrogen intake to maintain the integrity of our body. The average nitrogen introduction by aminoacids, both in free form and bound one another to form proteins, is easily calculated by dividing the weight of aminoacids or proteins to 6.5.

In 1942 Rose et al., having identified 10 aminoacids as indispensable for the growth of the rat, started applying this knowledge to human nutrition. Eight aminoacids were initially recognized as being indispensable to maintain the balance in studies which utilized the elimination of any single aminoacid from diet separately from the others, with the purpose of evaluating its impact on the overall body protein equilibrium.

These studies, if are fundamental to our knowledge of protein precursors (i.e. aminoacids) needs in a proper diet, were not lacking of important methodological mistakes, which have been then identified and understood.

This is why, for example, Rose concluded that histidine, an aminoacid which was found indispensable to the growth of rats, could be labeled as not indispensable for the maintenance of nitrogen balance in the adult man.

These works were so influential and the study protocol so complicated that only in 1975 the evidence was acquired that histidine is instead an indispensable aminoacid. For further information on the ten aminoacids nowadays recognized as indispensable to human needs of protein balance maintenance, see for example Stryer, Biochemistry, III Edition.

A wide literature is available, concerning the use of aminoacids.

For instance, from U.S. Pat. No. 4,670,261 a balanced parenteral alimentation solution is known, containing reducing sugars, essential aminoacids and electrolytes, and which does not discolour on sterilisation.

From EP-A-0 057 209 a composition is known, containing leucine, valine and isoleucine, for treating stress and injury, especially as parenteral feeding solution.

From DE-A-25 30 246 amino acid mixtures are also known, for treating kidney and liver disorders.

From DE-A-25 31 204 oral and parenteral amino acid solutions are known, containing essential and nonessential l-amino acids in specified proportions, having high nutritive values.

From JP-A-3 204 814 aminoacid preparations are known, for treatment of renal insufficiency, which comprises granule mixture coated with methacrylic copolymer, mixed with cellulose.

From EP-A-0 413 528 the treatment of skin conditions is known, by using compositions containing alpha hydroxy:acid, alpha keto:acid or polymeric hydroxyacid(s) and amphoteric agent.

The present invention is based on the acknowledgment of the fact that the need of nitrogen (i.e. of alimentary proteins, i.e. of aminoacids) is the product of a very complex whole of factors:

1) The quantities of proteins present in the body are subject to dimensional modifications according to adaptive needs. The most striking examples are the development of muscular hypertrophy in weight lifters, or hyper gamma-globulinemia in response to bacterial infections. Particular stress can, on the contrary, accelerate protein turnover, such as sun exposure, whose ultraviolet or infrared solar rays rapidly degrade skin collagens (see U.S. Pat. No. 5,198,465 in the name of Dioguardi, 1993) or a bad nutrition which leads to a weight and muscular loss.

2) A part of protein (i.e. aminoacids) input is utilized for energy purposes to balance inadequate glucose availability or to spare glucose, when this is required by specific metabolic needs, as in athletes during protracted efforts and/or in prolonged fasting and/or during a weight reduction, either because of dietary programs or of medical needs. It should be noticed that a ratio of 150 Kcal of carbohydrates is generally suggested to be assumed each 6.5 g. of aminoacids (that is to say each nitrogen gram), to achieve the maximal synthetic nitrogen utilization and to lower then aminoacidic losses for oxidative purposes (i.e. for energy). Some aminoacids are more suitable than others for these purposes (see for instance the above-mentioned Stryer, Biochemestry, III Edition).

3) The changes in alimentary habits due to cultural models, or to working rhythms or to ideal physical models, are very often, not in favor of a sufficiently complex and varied nutritional introduction. This, in turn, especially for aminoacids intake, could be obtained only if a very large amount of food (i.e. of calories) is introduced, (see for instance Tab. 4 in the following).

4) Current daily requirements of aliments are underestimated for different aminoacids, and calculated for a very sedentary theoretic individual, and consistent with mere survival and for a short time (some weeks), than for bearing an active life; thus they are very criticized by clinical nutritionists (see: European Journal of Clinical Nutrition Vol. 50, S2–S197 supplement-1 February 1996). Two situations are worthy of attention because even a careful nutrition may not be sufficient to body needs: for instance in pancreatectomized patients (e.g.: for pancreatic cancer) and in elderly people. In both cases, for different reasons, a reduction in digestive enzymes would be observed. Proteins, if not digested to aminoacids, could not be absorbed. Thus a malnutrition can occur even during a normal nutrition. Free aminoacids are instead absorbed without any contribution by the digestive system.

5) All aliments contain aminoacids in proportions not corresponding to specific human needs. Therefore, the bigger is the load of not utilized aminoacids, the bigger is the quantity of nitrogen disposal loads.

Disposal of nitrogen is based manly on an efficient kidney function, so for people depending on dialysis to maintain their life, the more usable is the aminoacidic content of diet, the less their body needs to eliminate nitrogen under the form of urea, thus contributing to a better compliance to alimentary introduction. This is a totally different approach from Giordano's one, who derived an aminoacidic formulation from the hypothesis that a mixture containing a reduced average of urea precursors aminoacids (mainly arginine and glutammine), when used as a nutritional device, would have led to a better nitrogen tolerance.

6) The only risk, traditionally mentioned by nutritionists, following the administration of large quantities of aminoacids, either as acute or chronic supplement to diet, is the well known effect of high nitrogen intakes on calcium balance (see, Kim Y, and Linkswiler H. M.: Effect of level of protein intake on calcium metabolism and on parathyroid and renal function in the adult human male Journal of Nutrition, 109, 1399–1404, 1979). There is no known aminoacid based formulation that can be expressly considered as safe in relationship to calcium metabolic losses, and at the same time being efficient so that it can refuel the body according to the said biological needs.

On the basis of the above considerations, the aim of the present invention is that of indicating compositions based on aminoacids that can enhance the maintenance of the equilibrium between synthesis and degradation of proteins, reducing the risks of under nutrition for some aminoacids and/or the risk of overload of those aminoacids less useful to nitrogen metabolism, still maintaining easily under control the caloric input.

Within the above general aim, a purpose of the present invention is that of indicating compositions of essential aminoacids suitable for use in all conditions where, due to the need of maintenance of a low caloric intake, protein anabolism should be implemented by elevated amounts of nitrogen compounds.

A second purpose of the present invention is that of indicating compositions of essential aminoacids suitable for use in all conditions where digestive enzymatic processes are inefficient to maintain normal nitrogen intake, thus compromising body protein dependent equilibrium.

A third purpose of the present invention is that of indicating compositions of essential aminoacids suitable for use in all conditions where the best maintenance of protein anabolism should be obtained with the minimal contribution from alimentary intake to nitrogen catabolism (urea, creatinine, uric acid).

According to the present invention, the above aim and purposes are reached by the compositions based on aminoacids, in particular essential aminoacids, that we have found as a result of our studies, and which has the characteristics specified in the annexed claims.

Further aims, characteristics and advantages of the compositions based on aminoacids, for preventing and treating inadequate aminoacidic introduction and/or overload of less needed aminoacids, without interfering with calcium metabolism, according to the present invention, will be clear from the following detailed description, which is supplied as a pure example.

The compositions according to the invention are based on aminoacids, and the ratios among aminoacids are consistent with the real needs of a stressed metabolism, as studied by the inventor, with the purposes both of feeding by a sufficient amount of aminoacids to cover all aminoacids needs and to give the lowest quantity of those necessary aminoacids that are utilized in metabolism, thus reducing the load on disposal system of the body by minimizing catabolic products (i.e. urea, uric acid, etc.), without altering calcium excretion, which is the main purpose of this special formulation, besides allowing the best nitrogen support according to body needs. Preferring excipients and diluents for systemic administration according to the invention, when needed are starchy carbohydrates and low molecular weight non starchy carbohydrates suitable for tablets and/or capsules preparations, or physiological (saline) or glucose 5–10% solutions for intravenous use.

The compositions according to the invention contain the following percentages by weight of the various components:

TABLE 1

| LEUCINE | up to 250 | up to 95% |
|---|---|---|
| ISOLEUCINE | up to 250 | of total weight |
| VALINE | up to 250 | |
| THREONINE | up to 125 | |
| LYSINE | up to 250 | |
| CISTINE | up to 50 | up to 25% |
| HISTIDINE | up to 50 | of total weight |
| PHENYLALANINE (– TIROSINE) | up to 50 | |
| METIONINE | up to 50 | |
| TRIPTOPHAN | up to 50 | |

Values are expressed as possible parts of 1000

Branched chain aminoacids (BCAA) needs have been identified by a huge literature, and a long term administration is needed, and of elevated quantities, when plasma concentrations should be raised in fasting conditions.

Because of their chemical-physical characteristics, being compounds that minimally influence pH in physiological conditions, they are defined "neutral" aminoacids, a specific branched chain aminoacids ratio in the mixture helps in maintaining a stable pH in physiological fluids. Threonine and lysine are present in larger quantities than the essential order of aminoacids, with the exception of the branched chain ones, because of the importance of their needs. This has been derived by studies dealing with aminoacids metabolic consumption during rigidly programmed physical stress conditions (Tab. 3), but the formula is at the same time adequate to the ratio of introduced aminoacids with the physiological daily urinary aminoacidic losses we have registered in large horizontal population studies, based on 24 hours urinary collection.

The amount of other essential aminoacids involved in synthetic processes is directly proportional to the quantity contained in proteins that need to be built. In table 2 the results are shown on BCAA, of an oral administration of 24 g of leucine, isoleucine and valine (in a ratio as shown in Tab. 1), supplementing normal diet in 12 volunteers.

TABLE 2

| | BASE | 1 MONTH | 3 MONTHS | 6 MONTHS | 12 MONTHS |
|---|---|---|---|---|---|
| LEUCINE | 100 ± 27 | 109 ± 35 | 118 ± 28* | 126 ± 26* | 137 ± 27* |
| ISO-LEUCINE | 62 ± 23 | 75 ± 26* | 78 ± 33* | 78 ± 26* | 81 ± 18* |
| VALINE | 177 ± 52 | 200 ± 51* | 228 ± 58* | 231 ± 48* | 233 ± 57* |

Values are expressed as per m mol/l.
n = 12
* = P < 0.05 or more

In studies performed with mixtures containing a total of 20 g of aminoacids, but distributed in 10 ratios of <2 g of aminoacids, no plasma modifications could be detected.

Plasma modifications of some aminoacids is highly desirable when specific metabolic pathways, aminoacids dependent, should be controlled. Indeed, nitrogen overloads are predicted to increase calcium urinary losses by mechanisms that have not been yet completely understood (see: Studies on the mechanism of protein induced hypercalciuria in older men and women, Schouette S. A. et al. Journal of Nutrition 110, 305–315, 1980).

The formulation presented in Tab. 1 was obtained by controlling that the effects programmed by its peculiar formula were attained in vivo. It was planned to induce no physical-chemical variation of urines theoretically incompatible with calcium tubular re-absorption. As an example, a particular attention has been used in planning that the presence of aminoacids would not alter urinary pH, if they were excreted in high quantities, as already said. The pH of the mixture according to the invention in distilled water was 6.82: this is the value we have identified experimentally as the best suitable for obtaining both a nutritionally more efficient composition and not influencing calcium excretion.

In Tab. 3 plasma concentrations of leucine are shown three hours before and after the loads. Urinary excretion of and urinary aminoacid concentrations and calciuria were measured. Urinary excretion of aminoacids is strictly dependent on plasma concentrations, being for any aminoacid always <10% of plasma concentration, both in urine samples in fasting conditions, and in those collected during and after the loads.

These data show that there is no urinary loss of aminoacids, and that no increased calcium losses is induced by ingestion of this formula of aminoacids, even at these very high dosages. Similar experiments have never been reported in literature before.

TABLE 3

| Plasma concentration (in mcg/ml) | basal | 180 minutes |
|---|---|---|
| LEUCINE | 15 ± 4.6 | 45 ± 22** |
| BCAA Total | 50 ± 14 | 190 ± 30** |
| Calcium Urinary concentrations mg in whole urinary output (6 hours) | 4.2 ± 3.6 | 3.1 ± 1.9 |

** = p < 0.005 or more

Moreover, in training athletes, a careful follow up of strenuous exercise showed a relevant consumption of some aminoacids (in particular leucine, isoleucine, valine, threonine, lysine), while other aminoacid concentrations rose as the product of muscular energetic consumption (i.e. useless aminoacids not needed to be introduced by aliments to prevent disposal overload), as shown for alanine in Tab. 4.

TABLE 4

|  | BASAL | AFTER 1 HOUR OF TRAINING |
|---|---|---|
| LEUCINE | 22 ± 3.8 | 18 ± 5.2* |
| ISOLEUCINE | 12 ± 2.6 | 9.4 ± 2.8* |
| VALINE | 36 ± 6.8 | 31 ± 7.8* |
| THREONINE | 17 ± 4 | 15 ± 3.6* |
| LYSINE | 31 ± 4.6 | 26 ± 5.7* |
| ALANINE | 40 ± 13 | 54 ± 19* |

T Test: P = p < 0.05 or more

Tracer studies have shown that daily requirements for branched chain aminoacids, threonine and lysine, are nowadays known to be underestimated for a factor ranging from two to five folds, and that branched chain aminoacids plus threonine and lysine cover two third of total nitrogen needs.

The correct ratio among leucine, isoleucine and valine (the branched chain aminoacids) plus threonine and lysine and the other essential aminoacids is therefore needed for covering adequately the real metabolic human needs without having to overload human body of calories and nitrogen.

Indeed just to meet a 24 g of the inventor's composition components, you will need:

TABLE 5

| 24 g of composition as expressed in Tab. 1 contains 96 Kcal, and is contained in | 3360 g whole milk (2186 Kcal) 283 g parmesan cheese (1123 Kcal) 665 g fillet beef (1567 Kcal) 648 g sea bass (595 Kcal) 1762 g white bread (4884 Kcal) |
|---|---|

Efficacy and safety of the mixture has been tested both by acute and by chronic administration.

Therefore we have tested 8 volunteers who ingested after an overnight fasting, 24 g. of the said mixture.

Plasma concentrations of leucine and of the sum of all three branched chain aminoacids (BCAA) are reported to test the absorption of the mixture, and calciuria dosed in specimens of urines obtained immediately before and 180 minutes after ingestion, showed no increase in calcium losses (see Tab. 3).

In ten volunteers who have followed a repetitive diet for fifteen days, by adding to their normal and balanced diet (prepared according to the World Health Organization) 24 g. per day (divided into three daily administrations of 8 g.) of the aminoacid mixture as shown in Tab. 1, calcium excretion has been studied by collecting the urines of 24 hours before and after the period of evaluation.

The results are shown in Tab. 6.

TABLE 6

|  | CALCEMIA M ± S.D. | CALCIUM EXCRETIONS: URINARY CALCIUM PLASMA CREATININE URINARY CREATININE |
|---|---|---|
| BASAL | 9.2 ± 0.5 | 0.117 ± 0.03 |
| AFTER 15 DAYS | 9 ± 0.8 | 0.104 ± 0.04 |

In the same group of volunteers the creatinine elimination by the urines has been studied as a marker of muscular protein degradation in order to test the effects on the muscular trophysm.

The results of the period of fifteen days of addition of 24 g. per day of the mixture as expressed in Tab. 1 have shown a reduction of the creatinine excretion, as per the following Tab. 7, clear evidence of muscular anabolism and/or reduction of the structural protein breakdown.

TABLE 7

| EXCRETION URINARY CREATININE MG % cL | |
|---|---|
| BASAL | 15 DAYS |
| 18.3 ± 1.9 | 13.9 ± 3.7* |

* = P < 0.05 or more

The whole of these data shows that even though a large nitrogen quantity had been added to the normal diet, the nitrogen catabolism had not increased, while there was not risk to increase calcium losses.

According to the above, the inventor has achieved a formulation of a composition based on aminoacids, in particular essential aminoacids, where the ratios among aminoacids are balanced according to the requirements of human metabolism, to achieve the maximal protein syntheses and minimal catabolic loads; said conditions are attained according to the invention by means of compositions comprising up to 75% of the branched chain aminoacids leucine, isoleucine and valine, and up to 50% of threonine and lysine; said compositions also contains up to 40% of aminoacids cistine, hystidine, phenylalanine, and thyrosine, methionine and triptophan. The preferred ratios are in particular:

from 20 to 75% of leucine, isoleucine and valine, in a ratio among them of 10 to 50% of leucine, 10 to 50% of isoleucine and 10 to 50% of valine;

from 10 to 50% of threonine and lysine, in a ratio among them of 10 to 55% of threonine and 10 to 75% of lysine;

up to 40% of cistine, hystidine, phenylalanine, and thyrosine, methionine and triptophan, in ratios from 0.5 to 50% among them.

Any other non-essential aminoacids could be summed to the above mixtures, without altering the positive effects, if in a percentage lower than 20% than the active ingredients. The formulation of the compositions prepared by the inventor have proved to overcome the limits of the known usual protein intake, meant as inadequate ratios to the real needs of the aminoacids among themselves, and to be safer than the protein intake with reference to calcium balance.

From the above, it results clear that the compositions based on aminoacids that we have found, according to the invention, are suitable to prevent and treat alimentary overloads in conditions of elevate body nitrogen requirements, without causing calcium losses.

Within this frame, the compositions according to the invention are suitable for use in all conditions where, due to the need of maintenance of a low caloric intake, protein anabolism should be implemented by elevated amounts of nitrogen compounds; this is the case of athletes.

Similarly, the compositions according to the invention are suitable for use in all conditions where digestive enzymatic processes are inefficient to maintain normal nitrogen intake, as in pancreatectomized patients and/or elders, where the body protein dependent equilibrium are compromised.

The compositions according to the invention are also suitable for use in all conditions where the best maintenance of protein anabolism should be obtained with the minimal contribution from alimentary intake to nitrogen catabolism (urea, creatinine, uric acid), as in patients with compromised renal functions.

From the given description the characteristic and advantages are therefore clear, of the compositions based on aminoacids according to the invention.

It is clear that several changes are possible for the skilled man to the compositions described by way of example, without departing from the novelty principles inherent to the invention. For instance, in the case of enteral use of a composition according to the invention, in the amount of diluents and excipients one or more compounds are in a ratio higher than 30% of the weight of the sum of the other components.

In the case of parenteral use of a composition according to the invention, in the amount of diluents and excipients one or more compounds are in a ratio higher than 50% of the weight of the sum of the components.

For oral use of a composition according to the invention, under the form of tablets, capsules, granules or powder, the amount of diluents and excipients, selected in the group consisting of starchy carbohydrates and non starchy carbohydrates, are in a ratio lower than 50% of the weight of the sum of the other components.

Finally, the compositions according to the invention can be used in all conditions where an essential aminoacids composition and supplementation may be physiologically or clinically useful for topic or external use and application; in this case, the amount of vehicles, diluents and exception, which can be selected in the groups consisting of ointments, creams, lotions, water-oily suspensions, gels or other compounds utilized for vehiculation by trasdermal devices, can be in ratio higher than 50% of the weight of the sum of the components.

What is claimed is:

1. A composition based on aminoacids for treating conditions of elevate body nitrogen requirements, without substantially altering calcium excretion and without substantially inducing a physical-chemical variation of urine which is theoretically incompatible with calcium tubular re-absorption and where, due to the need of maintenance of a low caloric intake, protein anabolism should be implemented by elevated amounts of nitrogen compounds, the composition comprising, as active ingredients:

up to 75% of the BCAA leucine, isoleucine and valine, up to 50% of threonine and lysine, up to 40% of cystine, histidine, phenylalanine, methionine, tryptophan, tyrosine, characterized in that threonine and lysine are present in larger quantities than the other essential aminoacids of the composition, with the exception of the BCAA of the composition.

2. A composition according to claim 1, characterized in that the ratios between said active ingredients is such that the composition generates a pH in water solution in the range of the physiological one, without the needs of PH stabilizing agents, such as reducing sugar.

3. A composition according to claim 1, characterized in that non-essential aminoacids are possibly in the composition, in a percentage being lower than 20% of said active ingredients.

4. A composition according to claim 1, characterized in that, for enteral use, in the amount of diluents and excipients one or more compounds are in a ratio higher than 30% of the weight of the sum of the other components.

5. A composition according to claim 1, characterized in that, for parenteral use, in the amount of diluents and excipients one or more compounds are in a ratio higher than 50% of the weight of the sum of the components.

6. A composition according to at least one of claim 1, characterized in that, for oral use under the form of tablets, capsules, granules or powder, the amount of diluents and excipients, selected in the group consisting of starchy carbohydrates and non starchy carbohydrates, are in a ratio lower than 50% of the weight of the sum of the other components.

7. A composition according to claim 1, characterized in that, for intravenous use, physiological or glucose solutions are provided as diluents and/or excipients.

8. A method for regulating nitrogen in a body, comprising administering thereto a composition comprising, as active ingredients:

up to 75% of the BCAA leucine, isoleucine and valine up to 50% of threonine and lysine up to 40% of one or more amino acids selected from the group consisting of cystine, histidine, phenylalanine, methionine, tryptophan, and tyrosine wherein threonine and lysine are present in larger quantities than the other essential amino acids of the composition, with the exception of the BCAA of the composition.

9. A method according to claim 8 further comprising administering said composition topically, said composition further consisting of inactive ingredients in an amount greater than 50 percent by weight of said composition, said inactive ingredients comprising one or more vehicles, diluents and excipients selected from the group consisting of ointments, creams, lotions, water-oily suspensions, gels and other compounds utilized for vehiculation by transdermal devices.

* * * * *